United States Patent [19]

Mann

[11] Patent Number: 5,665,360
[45] Date of Patent: Sep. 9, 1997

[54] METHOD OF TREATING PERIPHERAL NEUROPATHIES OF THE FEET AND LEGS

[76] Inventor: Richard H. Mann, 2047 SW. 36th Ave., Delray Beach, Fla. 33445

[21] Appl. No.: 528,999

[22] Filed: Sep. 15, 1995

Related U.S. Application Data

[63] Continuation of Ser. No. 61,020, May 14, 1993, abandoned.
[51] Int. Cl.⁶ .......................... A61K 35/78; A61K 39/385
[52] U.S. Cl. .......................................................... 424/195.1
[58] Field of Search ........................................... 424/195.1

[56] References Cited

PUBLICATIONS

Ortega Jimenez et al., Farm Clin 1990, vol. 7, n 1; 30–34 presented by applicant.
Chem. Abst. 113 (1990) 218098M.

*Primary Examiner*—Jerome D. Goldberg
*Attorney, Agent, or Firm*—Jenkens & Gilchrist

[57] ABSTRACT

Peripheral neuropathies associated with Diabetes Mellitus and infection with the AIDS virus may be treated effectively by the periodic topical application of a composition containing capsicum oleoresin as the active ingredient. The oleoresin is incorporated into a pharmaceutically acceptable carrier to form a lotion, ointment, cream or the like. When applied to the skin of the affected area at least daily, pain and burning associated with the neuropathy become reduced in severity or eliminated.

10 Claims, No Drawings

METHOD OF TREATING PERIPHERAL NEUROPATHIES OF THE FEET AND LEGS

This application is a continuation of application No. 08/061,020, filed on May 14, 1993, which was abandoned upon the filing hereof.

FIELD OF THE INVENTION

This invention relates to the use of capsicum oleoresin topical preparations for the treatment of distal peripheral neuropathies associated with diabetes and aquired immune deficiency syndrome (AIDS) and complex, for the relief of pain and burning sensations.

BACKGROUND OF THE INVENTION

Debilitating pain and burning sensations of the extremities may accompany diabetes, both insulin-dependent and non-insulin dependent, and also infection with the AIDS virus or its treatment.

U.S. Pat. No. 4,313,958 issued Feb. 2, 1982 to LaHann and U.S. Pat. No. 4,486,450 issued Dec. 4, 1984 to Bernstein disclose topical preparations of capsaicin (8-methyl-N-vanillyl-6-noneanamide) for producing analgesia in certain skin disorders. Capsaicin was first extracted from the fruit of the red pepper plant and is now also produced synthetically.

Capsicum oleoresin is a crude mixture of compounds, one of which is capsaicin, which may be produced by extraction of the fruit with solvents such as acetone. It has been used as a rubifacient or counterirritant, as has the powdered fruit in various compositions, U.S. Pat. No. 3,880,996 issued Apr. 29, 1975 to Fisher discloses a topical combination including salicylate analgesic in which it is demonstrated that the oleoresin, acting as a rubifacient, enhances the absorbtion of the analgesic. In U.S. Pat. No. 5,063,060 issued Nov. 5, 1991 to Bernstein, reference is made to other compounds, called capsinoids, in crude extracts of capsicum. He indicates that these are less effective than capsaicin.

Applicant has not met with complete success with the capsaicin compositions disclosed above in treating patients suffering from peripheral neuropathies associated with diabetes and AIDS.

SUMMARY OF THE INVENTION

It is thus an object of the invention to provide an effective topical treatment for peripheral neuropathies associated with diabetes and infection with AIDS virus. Despite the prior art observations that the non-capsaicin capsinoids were less effective than capsaicin, Application prepared some topical compositions with capsicum oleoresin as the active ingredient to test their effectiveness in treatment of these conditions in patients. Many plants, in their evolution of bioactive compounds, synthesize more than one single species of compound. These may each be more effective in their interaction with particular plants or animals. These may deter pests that would endanger successful reproduction. They may encourage animals to aid in their reproduction. For example, the red color and high vitamin C and D content may attract animals to eat the fruit and ingest the seeds. The irritant effect of the various capsinoids on the mucous membranes of different animals may cause the animal to spit out the seeds, thereby sowing seeds at a distance. Certain of the agents may cause irritability of the gut of certain animals so that the seeds pass to the stools before they can be digested.

Although this is mere speculation, it is not unusual to find that more than one compound in a plant has remarkable activity that is quite distinct from its evolutionary role. Consequently, Applicant considered the possibility that the crude oleoresin might have a combination of ingredients that would be more effective than the pure capsaicin.

This proved to be the case in certain applications. The capsicum oleoresin was incorporated as the sole active ingredient with various carriers well known in the pharmaceutical art to prepare creams, lotions, ointments and the like. These compositions were successfully employed for topical treatment of peripheral neuropathies, comprising applying the compositions to the affected skin in human patients to relieve the pain and burning as required.

DETAILED DESCRIPTION OF THE PREFERRED EMBODIMENTS

In the practice of the present invention, capsicum oleoresin is distributed in various pharmaceutically acceptable carriers such as lotions, creams and ointments for topical application in humans by techniques well known in the art. Some of these carriers contain volatile diluents such as alcohol, gylcols and the like and may also contain wetting agents, emulsifying and suspending agents as desired. Capsicum oleoresin was obtained from H. E. Daniels Co., Longfield Road, Turnbridge Wells, Kent, England. One batch #57425 contained 8% capsaicin by analysis. The proportion of capsaicin varies from batch to batch.

The compositions of the instant invention and the methods of their use will be more readily comprehended from the following examples.

EXAMPLES

Example I

A 64 year old white male with insulin dependent Diabetes Mellitus had chronic burning to his feet awakening him at night and constantly painful. A trial of capsaicin cream was not helpful.

An ointment was prepared from capsicum oleoresin having 1.5% capsaicin with the following composition:

| | |
|---|---|
| capsicum oleoresin | 50 grams |
| paraffin | 100 grams |
| petrolatum | 850 grams |

The ointment was applied to the painful areas three to four times a day for three to four weeks. Significant relief was felt within three weeks. The patient continues to apply the medicine in an ongoing manner with relief of the symptoms.

Example II

A 70 year old white male suffered from idiopathic neuropathy.

A lotion was prepared from capsicum oleoresin having 8% capsaicin with the following composition:

| | |
|---|---|
| capsicum oleoresin | 3.2 grams |
| 90% ethanol | 1 liter |

The lotion was applied to affected sites three times a day. He was much improved after three days, and significant relief increased over the next month to 90% improvement.

Example III

A 65 year old white mail with non-insulin-dependent Diabetes Mellitus and peripheral neuropathy affecting the toes and forefoot bilaterally has had chronic pain for 3 to 5 years.

The lotion of Example II was applied daily with great improvement over the next two to three weeks.

Example IV

An 85 year old white female with idiopathic neuropathy bilaterally to feet and legs with progressively increasing pain.

A lotion was prepared from capsicum oleoresin containing 8% capsaicin with the following composition:

| | |
|---|---|
| capsicum oleoresin | 9.6 grams |
| 90% ethanol | 1 liter |

The lotion was applied several times daily to the feet and legs. Marked improvement was noted within three weeks. Compositions containing between 0.25% and 7% oleoresin capsicum in various carriers have been found to be effective in this treatment method.

It is apparent that the inventive treatment of these disorders have been effective.

This invention may be embodied in other forms or carried out in other ways without departing from the spirit or essential characteristics thereof. The present disclosure is therefore to be considered illustrative and not restrictive, the scope of the invention being indicated by the appended claims, and all of the changes which come within the meaning and range of equivalency are to be embraced therein.

I claim:

1. A method of treating pain or burning sensations of peripheral neuropathies of the feet and legs due to infection with the acquired immune deficiency syndrome virus or associated with acquired immune deficiency syndrome treatments, the method comprising topically applying an effective amount of a capsicum oleoresin composition in a pharmaceutically acceptable carrier to the affected areas of the feet and legs for a time sufficient to relieve the symptoms due thereto, said composition comprising crude capsicum oleoresin.

2. The method of claim 1, wherein the composition is applied at least daily.

3. The method of claim 1, in which the composition is applied more than once daily.

4. The method of claim 1, wherein the oleoresin is present in an amount of not less than about 0.25% by weight of carrier.

5. The method of claim 1, wherein the oleoresin is present in the range from about 0.25% to about 50% by weight of carrier.

6. A method of treating pain or burning sensations of peripheral neuropathies of the feet and legs due to Diabetes Mellitus, the method comprising topically applying to the affected areas of the feet and legs an effective amount of a capsicum oleoresin composition in a pharmaceutically acceptable carrier for a time sufficient to relieve the symptoms due thereto, said composition comprising crude capsicum oleoresin.

7. The method of claim 6, wherein the composition is applied at least daily.

8. The method of claim 6, in which the composition is applied more than once daily.

9. The method of claim 6, wherein the oleoresin is present in an amount of not less than about 0.25% by weight of carrier.

10. The method of claim 6, wherein the oleoresin is present in the range from about 0.25% to about 50% by weight of carrier.

* * * * *

UNITED STATES PATENT AND TRADEMARK OFFICE
CERTIFICATE OF CORRECTION

PATENT NO. : 5,665,360
DATED : Sep. 9, 1997
INVENTOR(S) : Mann

It is certified that error appears in the above-identified patent and that said Letters Patent is hereby corrected as shown below:

Column 1, line 49    Replace "Application"
                     With --Applicant--

Column 2, line 64    Replace "mail"
                     With --male--

Signed and Sealed this

Seventh Day of April, 1998

Attest:

BRUCE LEHMAN

Attesting Officer    Commissioner of Patents and Trademarks